(12) United States Patent
Tabuchi et al.

(10) Patent No.: US 11,369,407 B2
(45) Date of Patent: Jun. 28, 2022

(54) METHOD OF OPERATING A TREATMENT TOOL

(71) Applicant: Olympus Corporation, Hachioji (JP)

(72) Inventors: Yasuhiro Tabuchi, Hino (JP); Yuya Hidaka, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 311 days.

(21) Appl. No.: 16/720,419

(22) Filed: Dec. 19, 2019

(65) Prior Publication Data

US 2020/0121349 A1 Apr. 23, 2020

Related U.S. Application Data

(63) Continuation of application No. PCT/JP2017/024660, filed on Jul. 5, 2017.

(51) Int. Cl.
*A61B 17/3205* (2006.01)
*A61B 17/32* (2006.01)
*A61B 18/12* (2006.01)
*A61B 18/14* (2006.01)

(52) U.S. Cl.
CPC ............ *A61B 17/32056* (2013.01); *A61B 17/320016* (2013.01); *A61B 2018/1253* (2013.01); *A61B 2018/141* (2013.01)

(58) Field of Classification Search
CPC ............ A61B 17/32056; A61B 17/320016
See application file for complete search history.

(56) References Cited

U.S. PATENT DOCUMENTS

| 4,643,187 A | 2/1987 | Okada |
| 2001/0053909 A1 | 12/2001 | Nakada et al. |
| 2004/0158124 A1* | 8/2004 | Okada .................... A61B 1/012 600/104 |

(Continued)

FOREIGN PATENT DOCUMENTS

| JP | S60-024834 A | 2/1985 |
| JP | H9-201367 A | 8/1997 |

(Continued)

OTHER PUBLICATIONS

Sep. 19, 2017 International Search Report issued in Japanese Patent Application No. PCT/JP2017/024660.

(Continued)

*Primary Examiner* — Wade Miles
(74) *Attorney, Agent, or Firm* — Oliff PLC (57) ABSTRACT

The disclosed technology is directed to a method of operating a treatment tool for excising a lesioned portion of a body tissue. The method comprises applying a treatment tool to the lesioned portion. The treatment tool includes an elongated sheath having a snare wire disposed therein. The snare wire is configured to be movable forward or backward along a longitudinal direction. Next, forming the snare wire into a loop and tilting the loop in a plane transverse to the longitudinal axis of the elongated sheath with a force tending to push a snare wire portion out of a distal-end opening of the elongated sheath. And finally, placing the loop around the lesioned portion of the body tissue to excise the lesioned portion in a state in which the snare wire positioned transverse to the lesioned portion.

5 Claims, 10 Drawing Sheets

(56) References Cited

U.S. PATENT DOCUMENTS

| | | |
|---|---|---|
| 2008/0215064 A1 | 9/2008 | Motosugi |
| 2009/0076319 A1 | 3/2009 | Muyari |
| 2017/0112569 A1 | 4/2017 | Motosugi et al. |

FOREIGN PATENT DOCUMENTS

| | | |
|---|---|---|
| JP | 2002-45369 A | 2/2002 |
| JP | 2008-73317 A | 4/2008 |
| JP | 2009-072215 A | 4/2009 |
| JP | 2011-218771 A | 11/2011 |
| WO | 2013064577 A2 | 5/2013 |
| WO | 2016/080093 A1 | 5/2016 |

OTHER PUBLICATIONS

Sep. 19, 2017 Written Opinion issued in Japanese Patent Application No. PCT/JP2017/024660.

* cited by examiner

METHOD OF OPERATING A TREATMENT TOOL

CROSS-REFERENCE TO RELATED APPLICATION

This application is a continuation application of PCT Application No. PCT/JP 2017/024660 filed on Jul. 5, 2017, which is hereby incorporated by reference in its entirety.

TECHNICAL FIELD

The disclosed technology relates to an endoscopic treatment tool.

DESCRIPTION OF THE RELATED ART

One known endoscopic treatment tool for excising a lesioned portion using an endoscope operates by pushing a wire out of a distal end of a flexible sheath to spread the wire into a loop with the lesioned portion placed therein, and thereafter pulling the wire at a user side of the sheath to tighten the lesioned portion, after which a high-frequency electric current is passed through the wire as disclosed in the Japanese Patent Laid-open No. Hei 9-201367 (PTL 1).

With the endoscopic treatment tool, when the wire is advanced in the sheath, a binding member by which the wire is made into the loop abuts against a stopper fixedly disposed in the sheath, after which only one leg of the wire that is movably supported by the binding member is advanced and pushed out forwardly of the sheath, forming a semicircular loop in front of the sheath.

With the endoscopic treatment tool disclosed in PTL 1, however, the loop that is spread in front of the sheath spreads along a plane including the longitudinal axis of the sheath. In a case where the longitudinal axis of the sheath is disposed at an angle near a right angle with respect to the lesioned portion to be excised, it is difficult to place the loop in surrounding relation to the lesioned portion.

BRIEF SUMMARY OF EMBODIMENTS

The disclosed technology has been made in view of the problem described hereinbefore.

The disclosed technology is directed to a method of operating a treatment tool for excising a lesioned portion of a body tissue. The method comprises applying a treatment tool to the lesioned portion. The treatment tool includes an elongated sheath having a snare wire disposed therein. The snare wire is configured to be movable forward or backward along a longitudinal direction. Next, forming the snare wire into a loop and tilting the loop in a plane transverse to the longitudinal axis of the elongated sheath with a force tending to push a snare wire portion out of a distal-end opening of the elongated sheath. And finally, placing the loop around the lesioned portion of the body tissue to excise the lesioned portion in a state in which the snare wire positioned transverse to the lesioned portion.

Another aspect of the disclosed technology is directed to a method of operating a treatment tool for excising a lesioned portion of a body tissue. The method comprises applying a treatment tool to the lesioned portion. The treatment tool includes an elongated sheath having a snare wire disposed therein. The snare wire is capable of moving forward or backward along a longitudinal direction. Next, forming the snare wire into a loop and tilting the loop in a plane transverse to the longitudinal axis of the elongated sheath with a force tending to push a snare wire portion out of a distal-end opening of the elongated sheath so that the snare wire functions as a cantilever with the pushing force acting on the distal-end and is curved. And finally, placing the loop around the lesioned portion of the body tissue to excise the lesioned portion in a state in which the snare wire positioned transverse to the lesioned portion.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed technology to provide an endoscopic treatment tool that is capable of easily placing a loop around a lesion portion to be excised even in a case where the lesion portion is disposed in a direction transverse to the longitudinal axis of an elongated sheath, so that the endoscopic treatment tool can easily excise the lesion portion.

An endoscopic treatment tool 1 according to an embodiment of the disclosed technology will hereinafter be described with reference to the drawings.

Figure 1:
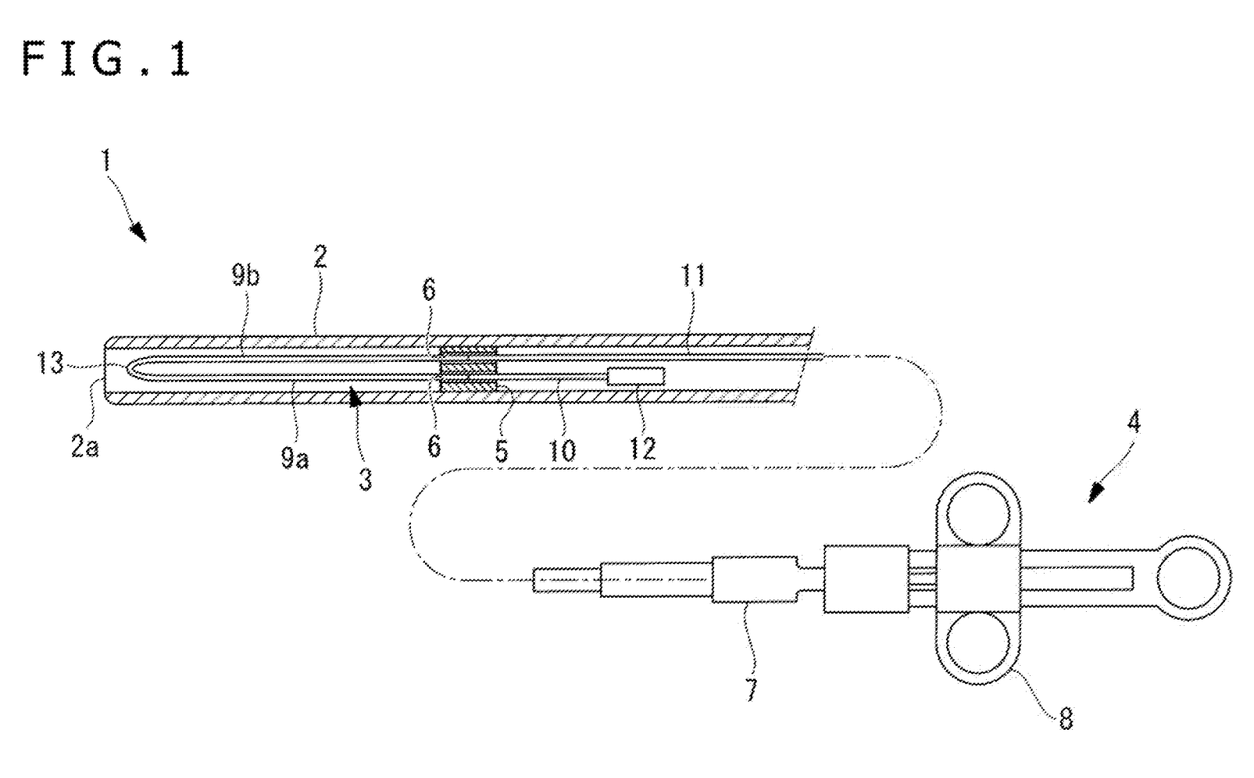
FIG. 1 is an overall makeup view illustrating an endoscopic treatment tool according to an embodiment of the disclosed technology.

As illustrated in FIG. 1, the endoscopic treatment tool 1 according to the present embodiment includes an elongated flexible tubular sheath 2, a wire 3 longitudinally movably inserted in the elongated sheath 2, and an operating portion 4 for operating the wire 3.

Figure 9A:
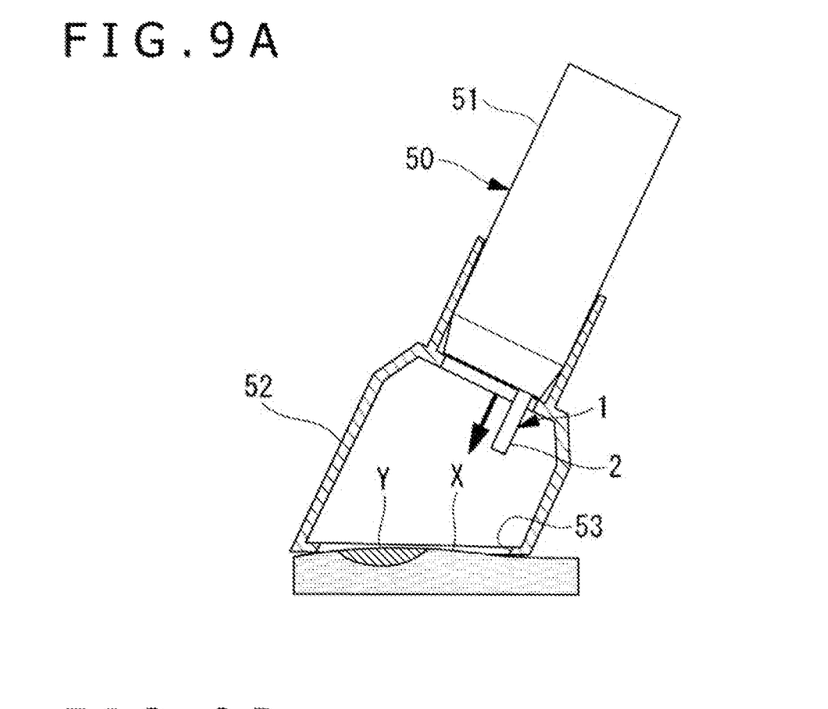
FIG. 9A is a longitudinal cross-sectional view illustrating a state in which a distal-end opening of a transparent cap mounted on a distal end of an endoscope is held in intimate contact with a biotissue and the cap is evacuated in EMRC.
Figure 9B:
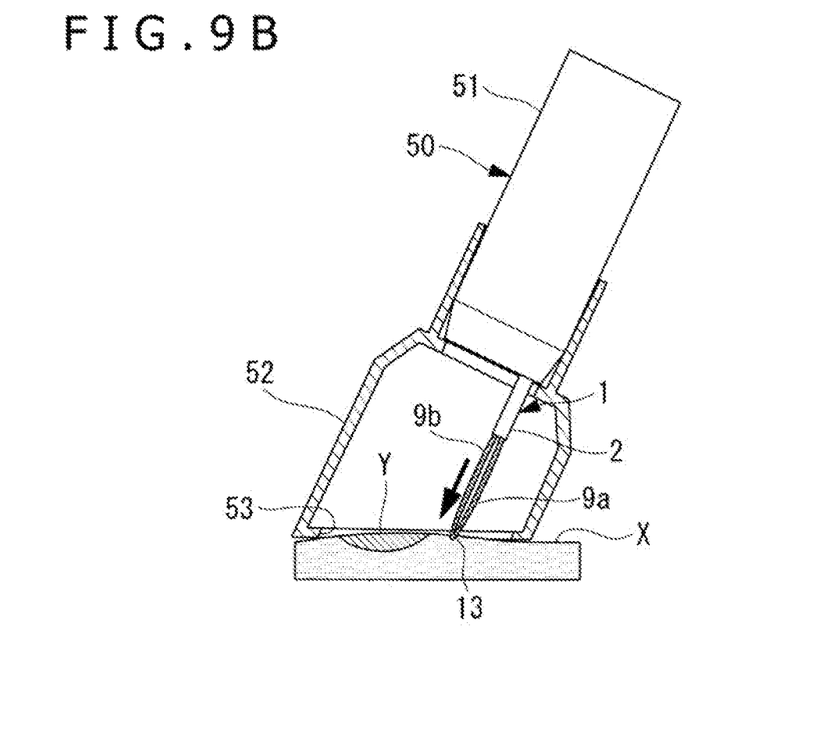
FIG. 9B is a longitudinal cross-sectional view illustrating a state in which a distal-end portion of the endoscopic treatment tool according to the present embodiment is introduced into the cap through a channel in the endoscope in the state illustrated in FIG. 9A.
Figure 9C:
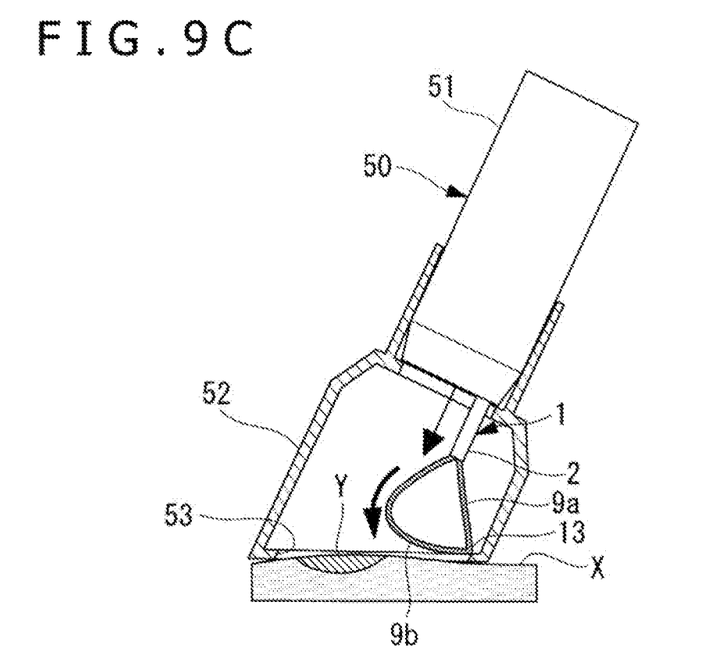
FIG. 9C is a longitudinal cross-sectional view illustrating a state in which a second snare wire portion is pushed out from the state illustrated in FIG. 9B.
Figure 9D:
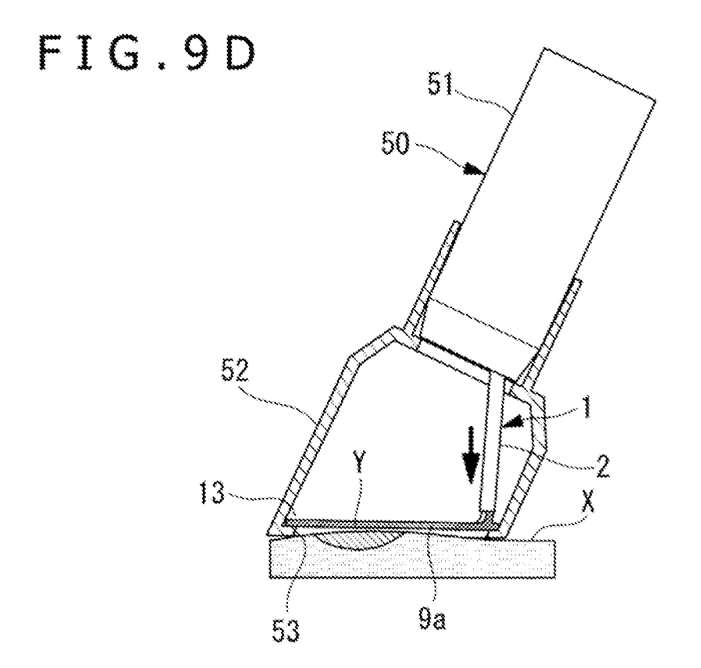
FIG. 9D is a longitudinal cross-sectional view illustrating a state in which the second snare wire portion is further pushed out from the state illustrated in FIG. 9C, causing a loop transverse to the elongated sheath to surround a lesioned portion.

The elongated sheath 2 has outer dimensions insertable into a channel in an insertion portion 51 (see FIG. 9A) of an endoscope 50.

As illustrated in FIG. 1, a stopper 5 is disposed at a longitudinally intermediate position in the elongated sheath 2. The stopper 5 has two through holes 6 defined therein that have such a diameter that a first operating wire 10, i.e., a first operating wire portion, and a second operating wire 11, i.e., a second operating wire portion, to be described hereinafter, can extend therethrough, but a movable body 12 cannot pass therethrough.

As illustrated in FIG. 1, the operating portion 4 includes a main operating portion body 7 to which a proximal end of the elongated sheath 2 is attached and a slider movably mounted on the main operating portion body 7 for movement in the longitudinal directions of the elongated sheath 2. The second operating wire 11, to be described hereinafter, has a proximal end connected to the slider 8.

Figure 2:
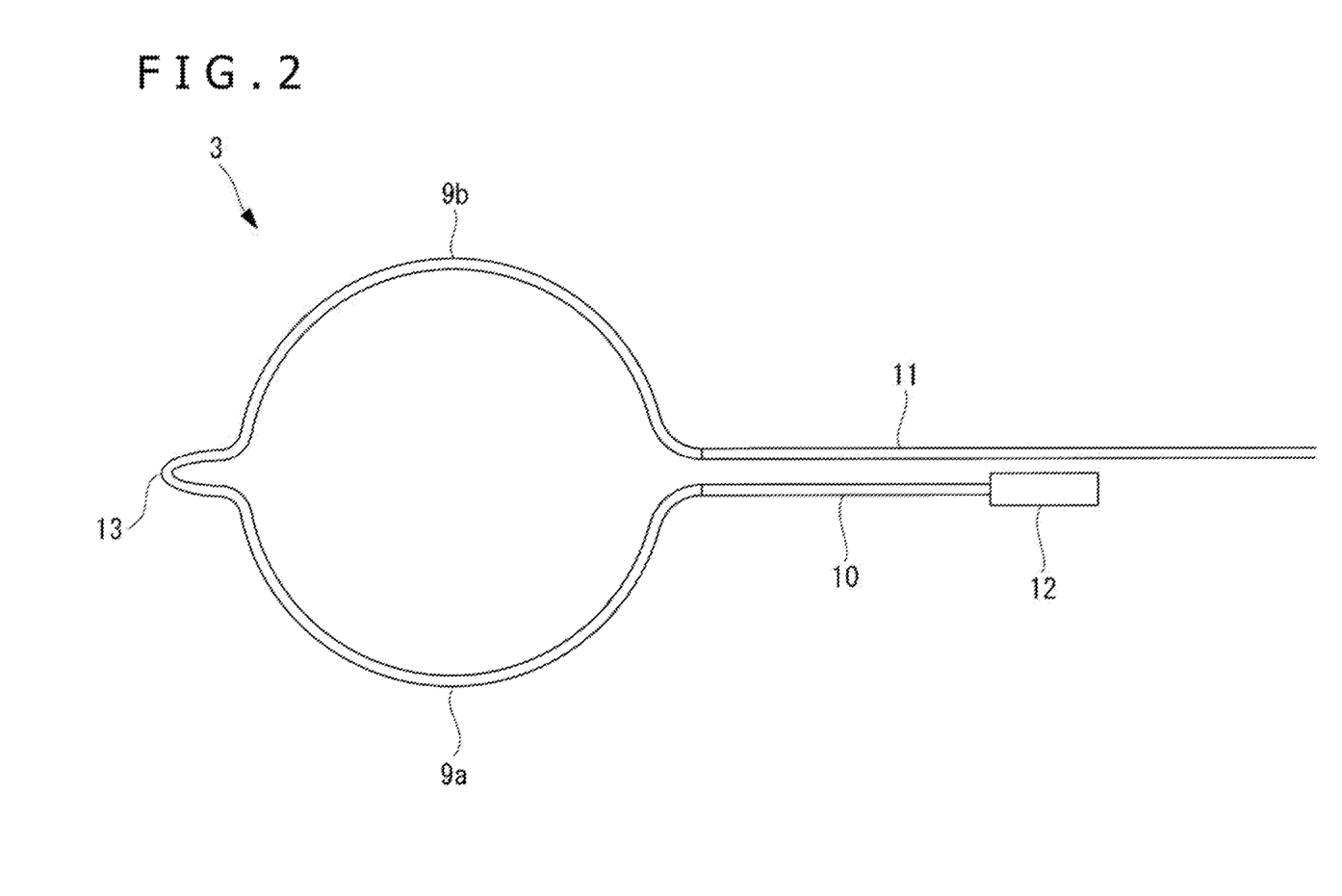
FIG. 2 is a view illustrating a wire of the endoscopic treatment tool illustrated in FIG. 1.

The wire 3 is made up of twisted strands. As illustrated in FIG. 2, the wire 3 includes snare wires 9a and 9b, i.e., snare wire portions, having a folded portion 13 that is folded back over itself, forming a protrusion when the snare wires 9a and 9b are spread into a loop, and a first operating wire 10 and a second operating wire 11 that are connected respectively to two ends of the snare wires 9a and 9b. According to the present embodiment, a monopolar electrode that is a high-frequency electrode is used as the snare wires 9a and 9b.

The movable body 12 that is disposed closer to a proximal-end side than the stopper 5 is attached to a proximal end of the first operating wire 10. When the first operating wire 10 that is disposed through one of the through holes 6 in the stopper 5 is advanced along a longitudinal direction of the elongated sheath 2, the movable body 12 abuts against a proximal-end face of the stopper 5 and is stopped from being further advanced.

The position of the stopper 5 in the longitudinal directions of the elongated sheath 2 and the length of the first operating wire 10 up to the movable body 12 are set such that when the movable body 12 abuts against the proximal-end face of the stopper 5, the snare wire 9a, hereinafter referred to as "first snare wire portion," disposed between the first operating wire 10 and the folded portion 13 projects forwardly from a distal-end opening 2a of the elongated sheath 2 by a length that operates in the manner to be described hereinafter.

Figure 3:
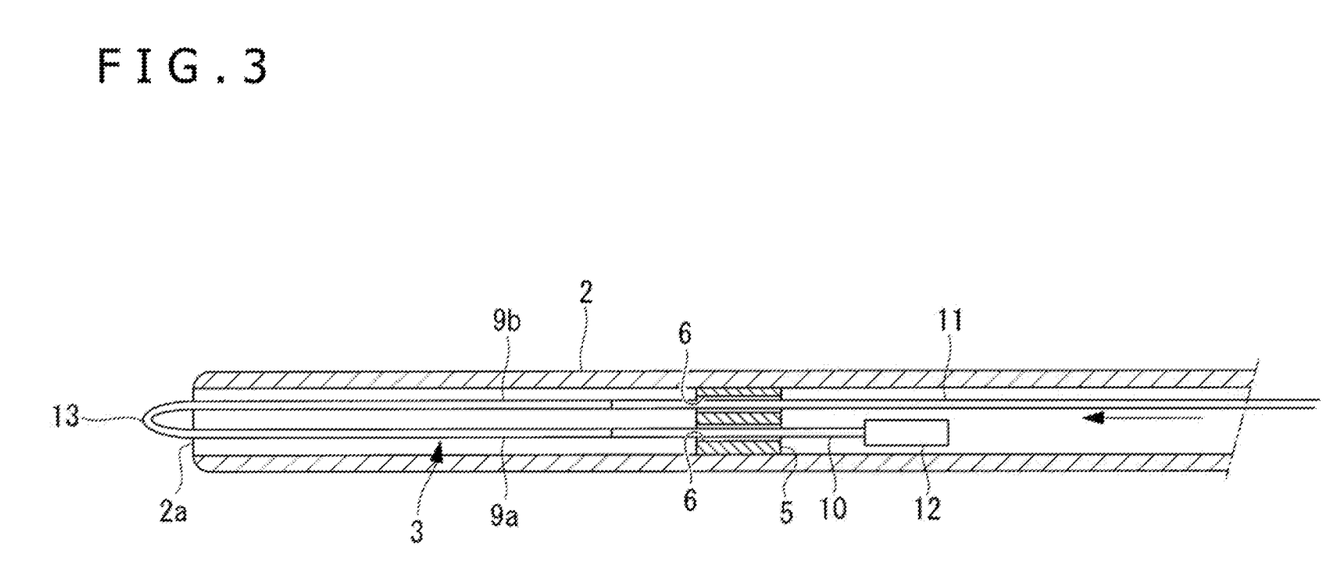
FIG. 3 is a longitudinal cross-sectional view illustrating a state in which the wire illustrated in FIG. 2 is being advanced in its entirety in a sheath.
Figure 4:
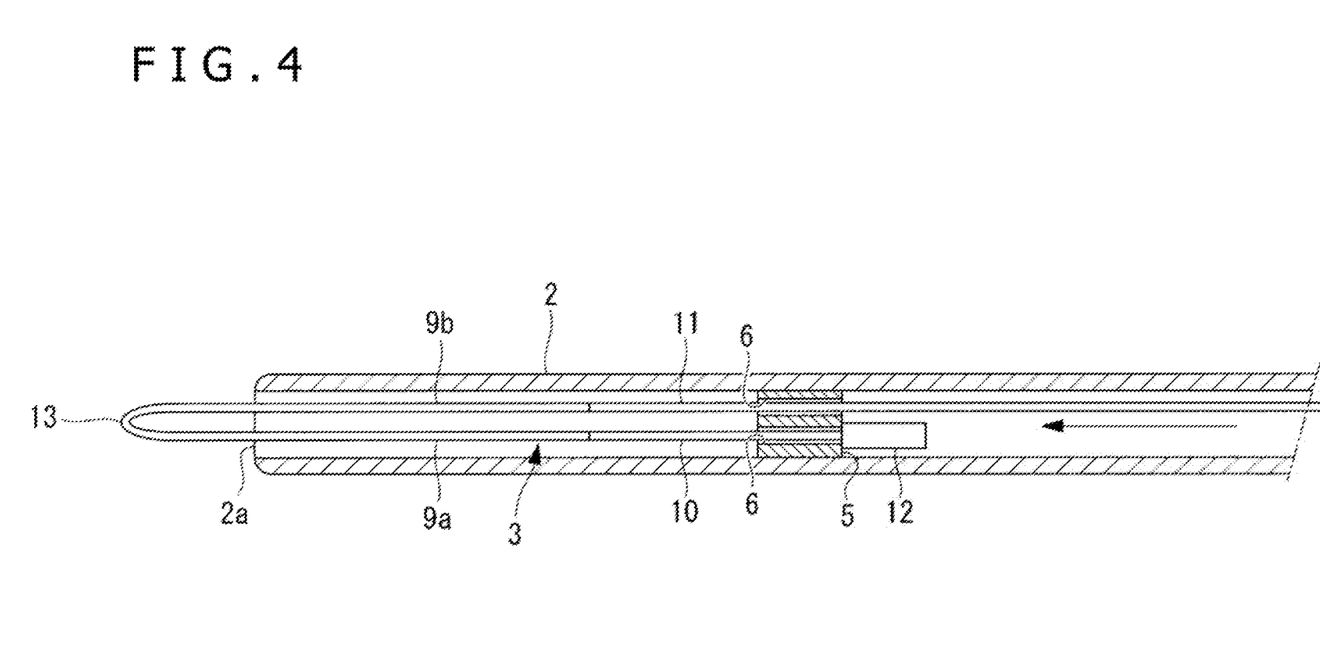
FIG. 4 is a longitudinal cross-sectional view illustrating a state in which a movable body has abut against a stopper illustrated in FIG. 1.

Specifically, with the endoscopic treatment tool 1 according to the present embodiment, when the second operating wire 11 connected to the slider 8 is pushed out forwardly by advancing the slider 8 with respect to the main operating portion body 7, the wire 3 in its entirety is moved forwardly along a longitudinal direction in the elongated sheath 2, as illustrated in FIG. 3. Then, at the time the first snare wire portion 9a is exposed forwardly out of the distal-end opening 2a of the elongated sheath 2 by a predetermined length, as illustrated in FIG. 4, the movable body 12 abuts against the proximal-end face of the stopper 5.

Figure 5:
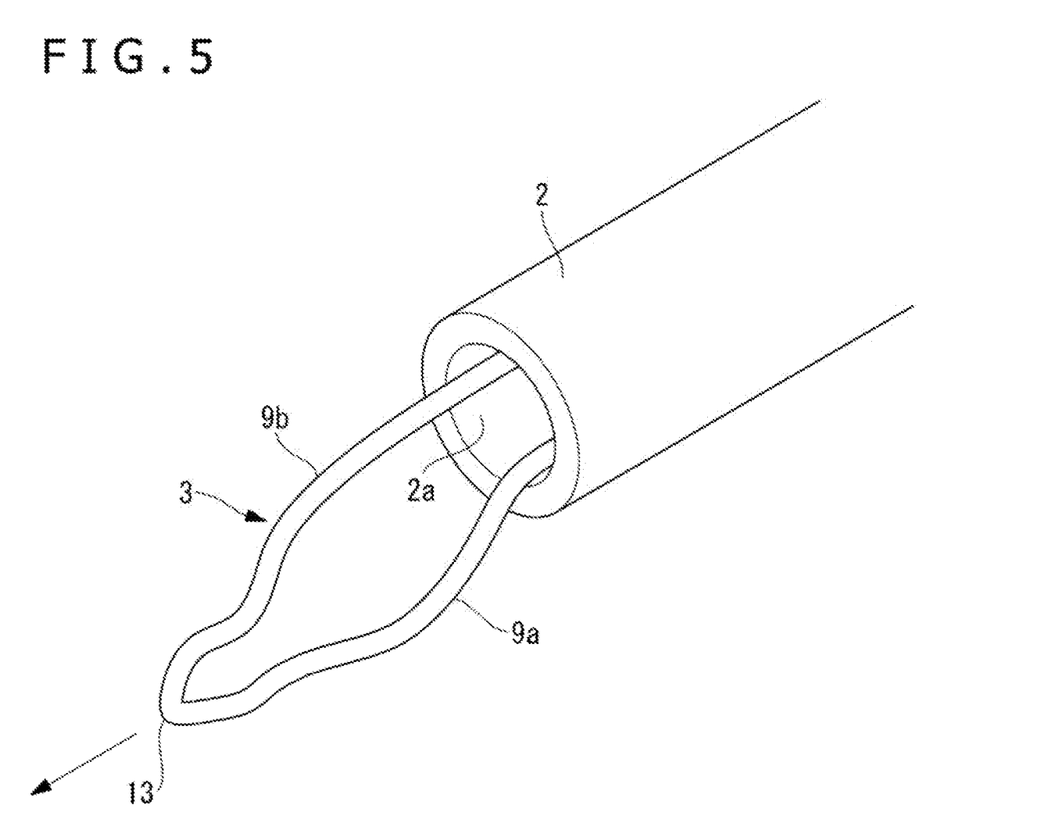
FIG. 5 is a perspective view of a distal-end portion of the elongated sheath in the state illustrated in FIG. 4.
Figure 6:
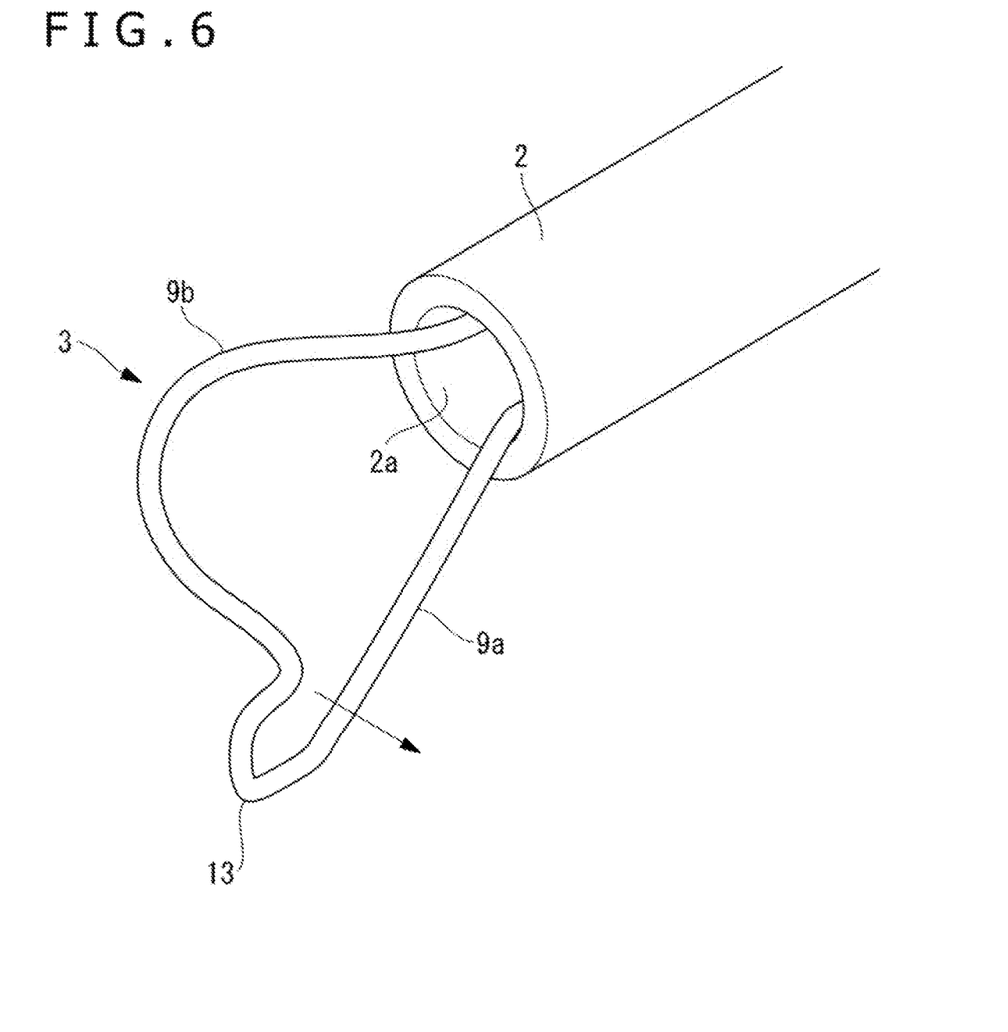
FIG. 6 is a perspective view illustrating a state in which only a second snare wire portion is pushed out after the state illustrated in FIG. 5.

Thereafter, by continuously advancing the slider 8, only the second operating wire 11 continues to be pushed out, as illustrated in FIG. 5, so that only the snare wire 9b, hereinafter referred to as "second snare wire portion," between the folded portion 13 and the second operating wire 11 continues to be pushed out of the distal-end opening 2a of the elongated sheath 2. The pushing force applied through the second operating wire 11 to the second snare wire portion 9b is transmitted to the first snare wire portion 9a at the folded portion 13. As a result, the first snare wire portion 9a exposed out of the distal-end opening 2a of the elongated sheath 2 functions as a cantilever with the pushing force acting on its distal end, and is curved.

At this time, in a case where the portion of the first snare wire portion 9a that functions as a cantilever is sufficiently short, the flexural rigidity of the cantilever becomes large enough to cause the pushing force applied to the distal end to act to deform a less rigid portion. Specifically, the pushing force tends to deform the first snare wire portion 9a made up of twisted strands in a direction to untwist the strands.

Figure 7:
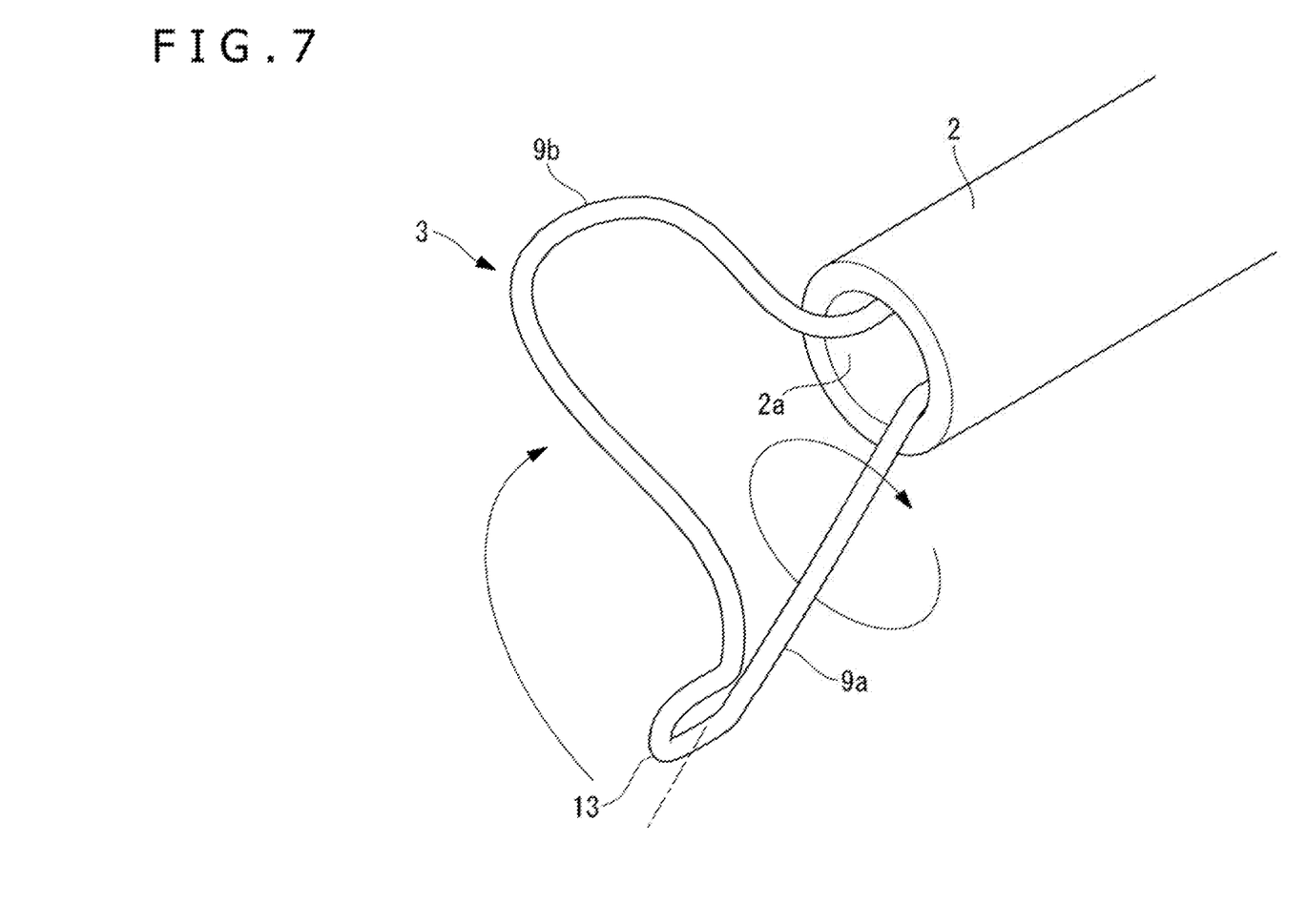
FIG. 7 is a perspective view illustrating a state in which a distal end of the second snare wire portion is turned substantially about the longitudinal axis of a first snare wire portion.
Figure 8:
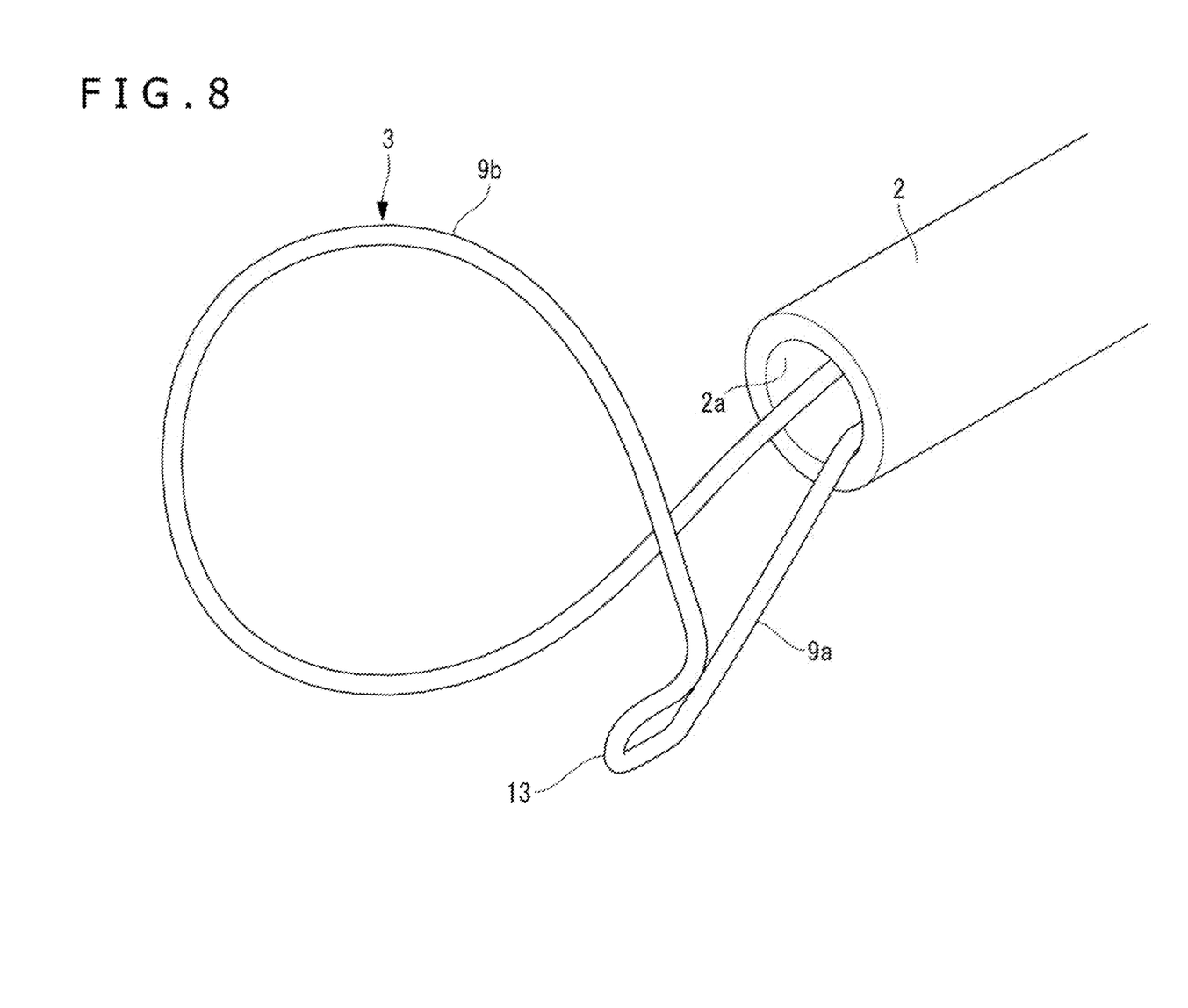
FIG. 8 is a perspective view illustrating a state in which the second snare wire portion forms a loop in a plane transverse to the longitudinal axis of the elongated sheath.

Therefore, as the first snare wire portion 9a is deformed in the direction to untwist its strands by the pushing force applied to the second snare wire portion 9b, a distal-end portion of the second snare wire portion 9b is turned substantially around the longitudinal axis of the first snare wire portion 9a, as illustrated in FIG. 7. As a consequence, when the operator only moves the slider 8 with respect to the main operating portion body 7 in a direction to push out the second snare wire portion 9b, the second snare wire portion 9b is continuously pushed out of the distal-end opening 2a of the elongated sheath 2 while turning the distal-end portion thereof, forming a loop that spreads along a plane transverse to the longitudinal axis of the elongated sheath 2, as illustrated in FIG. 8.

Consequently, the endoscopic treatment tool 1 according to the present embodiment is advantageous in that even if the elongated sheath 2 is disposed in a direction transverse to a surface of a biotissue X (see FIGS. 9A through 9D) having a lesioned portion Y, it is possible to form a loop and placing the loop easily around the lesioned portion Y by bringing the snare wires 9a and 9b protruding from the distal-end opening 2a of the elongated sheath 2 along the surface of the biotissue X.

Particularly, as illustrated in FIGS. 9A through 9D, the endoscopic treatment tool lends itself to an endoscopic mucosal resection using a cap-fitted panendoscope (EMRC) in which a transparent tubular cap 52 is mounted on a distal end of the insertion portion 51 of the endoscope 50, a distal-end opening 53 of the cap 52 is pressed against the biotissue X at a position around the lesioned portion Y, and the cap 52 is evacuated to draw the lesioned portion Y by suction and excised by the snare wires 9a and 9b. Specifically, even if the elongated sheath 2 is introduced through a channel in the endoscope 50 that is disposed in a posture transverse to the surface of the biotissue X in order to keep the distal-end opening 53 of the cap 52 in intimate contact with the biotissue X, it is possible to place the snare wires 9*a* and 9*b* along the biotissue X in the cap 52 in a position surrounding the lesioned portion Y simply by operating the operating portion 4 to push out the wire 3.

After the operating portion 4 is operated to tighten the periphery of the lesioned portion Y, a high-frequency electric current is passed through the wire 3 to excise the lesioned portion Y with ease.

The longer the distance by which the first snare wire portion 9*a* protrudes from the distal end of the elongated sheath 2 is, the smaller the flexural rigidity of the first snare wire portion 9*a* becomes. Therefore, since the action of the second snare wire portion 9*b* to turn around the longitudinal axis of the first snare wire portion 9*a* is less likely to occur, the snare wires 9*a* and 9*b* tend to spread into a loop along a plane along the longitudinal axis of the elongated sheath 2.

With the endoscopic treatment tool 1 according to the present embodiment, therefore, by having the first snare wire portion 9*a* protrude forwardly of the elongated sheath 2 by such a length that the flexural rigidity becomes higher than the rigidity, i.e., torsional rigidity, in a direction to untwist the snare wires 9*a* and 9*b* made up of twisted strands, that is, by a sufficiently short length, the snare wire portions 9*a* and 9*b* can spread into a loop in a plane transverse to the longitudinal axis of the elongated sheath 2 simply by pushing out the second operating wire 11.

Particularly, by having the second snare wire portion 9*b* protrude by at least twice the length of the first snare wire portion 9*a* that protrudes, the snare wire portions 9*a* and 9*b* can spread more easily into a loop in a plane transverse to the longitudinal axis of the elongated sheath 2.

Inasmuch as the elongated sheath 2 is made of a flexible material, it may be inserted into a channel in a soft endoscope while attaining the advantages described hereinbefore. In a case where the endoscopic treatment tool 1 is used with a hard endoscope, the elongated sheath 2 may be made of a hard material.

According to the present embodiment, the first operating wire 10 is connected to the first snare wire portion 9*a*, and the second operating wire 11 is connected to the second snare wire portion 9*b*. However, they may be integral with each other. Furthermore, the first snare wire portion 9*a* and the first operating wire 10 may be integral with each other, whereas the second snare wire portion 9*b* and the second operating wire 11 may be separate from each other, or the first snare wire portion 9*a* and the first operating wire 10 may be separate from each other, whereas the second snare wire portion 9*b* and the second operating wire 11 may be integral with each other.

In sum, the disclosed technology is directed to a method of operating a treatment tool for excising a lesioned portion of a body tissue. The method comprises applying a treatment tool to the lesioned portion. The treatment tool includes an elongated sheath having a snare wire disposed therein. The snare wire is configured to be movable forward or backward along a longitudinal direction. Next, forming the snare wire into a loop and tilting the loop in a plane transverse to the longitudinal axis of the elongated sheath with a force tending to push a snare wire portion out of a distal-end opening of the elongated sheath. And finally, placing the loop around the lesioned portion of the body tissue to excise the lesioned portion in a state in which the snare wire positioned transverse to the lesioned portion.

The method of operating the treatment tool includes a first operating wire portion is connected to a first end of the snare wire and configured to be movable in the longitudinal direction in the elongated sheath. A second operating wire portion is connected to a second end of the snare wire and movable in the longitudinal direction in the elongated sheath. A stopper having a hole through which the first operating wire portion passes and is fixedly mounted in the elongated sheath and a movable body is attached to the first operating wire side closer to a distal-end portion than the stopper side and having a width larger than an inside diameter of the hole. The snare wire includes a folded portion folded back onto itself forming a protrusion. A first snare wire portion is disposed between the first operating wire portion and the folded portion. A second snare wire portion is disposed between the second operating wire portion and the folded portion and wherein the method comprises pushing the second snare wire portion out of the distal-end opening of the sheath while the movable body is abutting against a proximal-end face of the stopper, thereby forming the second snare wire portion into the loop and tiling the loop in the plane transverse to the longitudinal axis of the elongated sheath while deforming the first snare wire portion. The method of operating the treatment tool further comprises turning the first snare wire portion around a longitudinal axis of the first snare wire portion while being curved when the loop is tilted in the plane transverse to the longitudinal axis of the sheath.

Another aspect of the disclosed technology is directed to a method of operating a treatment tool for excising a lesioned portion of a body tissue. The method comprises applying a treatment tool to the lesioned portion. The treatment tool includes an elongated sheath having a snare wire disposed therein. The snare wire is capable of moving forward or backward along a longitudinal direction. Next, forming the snare wire into a loop and tilting the loop in a plane transverse to the longitudinal axis of the elongated sheath with a force tending to push a snare wire portion out of a distal-end opening of the elongated sheath so that the snare wire functions as a cantilever with the pushing force acting on the distal-end and is curved. And finally, placing the loop around the lesioned portion of the body tissue to excise the lesioned portion in a state in which the snare wire positioned transverse to the lesioned portion.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A method of operating a treatment tool for excising a lesioned portion of a body tissue, the method comprising:
   applying a treatment tool to the lesioned portion, the treatment tool including an elongated sheath having a snare wire disposed in the elongated sheath, the snare wire being configured to move forward and backward along a longitudinal direction, the snare wire being formed of a plurality of twisted strands;
   forming the snare wire into a loop and deforming the snare wire in a direction to untwist the plurality of twisted strands to tilt the loop in a plane transverse to a longitudinal axis of the elongated sheath by a force pushing a portion of the snare wire out of a distal-end opening of the elongated sheath; and
   placing the loop around the lesioned portion of the body tissue to excise the lesioned portion in a state in which the snare wire is positioned transverse to the lesioned portion.

2. The method of claim 1, wherein:
   the treatment tool includes:
      a first operating wire portion connected to a first end of the snare wire and configured to be movable in the longitudinal direction in the elongated sheath,
      a second operating wire portion connected to a second end of the snare wire and configured to be movable in the longitudinal direction in the elongated sheath,
      a stopper having a hole through which the first operating wire portion passes and is fixedly mounted in the elongated sheath, and
      a movable body attached to the first operating wire side closer to a distal-end portion than the stopper side and having a width larger than an inside diameter of the hole,
   the snare wire includes:
      a folded portion folded back onto itself, forming a protrusion,
      a first snare wire portion disposed between the first operating wire portion and the folded portion, and
      a second snare wire portion disposed between the second operating wire portion and the folded portion, and
   the method further comprises:
      pushing the second snare wire portion out of the distal-end opening of the elongated sheath while the movable body is abutting against a proximal-end face of the stopper, thereby forming the second snare wire portion into the loop and tiling the loop in the plane transverse to the longitudinal axis of the elongated sheath while deforming the first snare wire portion.

3. The method of claim 2, further comprising rotating the first snare wire portion around a longitudinal axis of the first snare wire portion while being curved when the loop is tilted in the plane transverse to the longitudinal axis of the elongated sheath.

4. A method of operating a treatment tool for excising a lesioned portion of a body tissue, the method comprising:
   applying a treatment tool to the lesioned portion, the treatment tool including an elongated sheath having a snare wire disposed in the elongated sheath, the snare wire configured to move forward and backward along a longitudinal direction, the snare wire being formed of a plurality of twisted strands;
   forming the snare wire into a loop and deforming the snare wire in a direction to untwist the plurality of twisted strands to tilt the loop in a plane transverse to a longitudinal axis of the elongated sheath by a force pushing a portion of the snare wire out of a distal-end opening of the elongated sheath so that the snare wire functions as a cantilever with the pushing force acting on a distal end and is curved; and
   placing the loop around the lesioned portion of the body tissue to excise the lesioned portion in a state in which the snare wire is positioned transverse to the lesioned portion.

5. A method of operating a treatment tool for excising a lesioned portion of a body tissue, the method comprising:
   applying a treatment tool to the lesioned portion, the treatment tool including an elongated sheath having a snare wire disposed in the elongated sheath, the snare wire being configured to move forward and backward along a longitudinal direction, the snare wire being formed of a plurality of twisted strands that is twisted in a first rotational direction;
   forming the snare wire into a loop and deforming the snare wire in a second rotational direction, which is opposite to the first rotational direction, to tilt the loop in a plane transverse to a longitudinal axis of the elongated sheath by a force pushing a portion of the snare wire out of a distal-end opening of the elongated sheath; and
   placing the loop around the lesioned portion of the body tissue to excise the lesioned portion in a state in which the snare wire is positioned transverse to the lesioned portion.

* * * * *